(12) United States Patent
During et al.

(10) Patent No.: US 9,399,034 B1
(45) Date of Patent: Jul. 26, 2016

(54) METHODS OF SEDATION DURING CRITICAL CARE TREATMENT

(71) Applicant: Ovid Therapeutics Inc., New York, NY (US)

(72) Inventors: Matthew During, Weston, CT (US); Anna Kazanchyan, White Plains, NY (US)

(73) Assignee: OVID THERAPEUTICS INC, New York, NY (US)

( * ) Notice: Subject to any disclaimer, the term of this patent is extended or adjusted under 35 U.S.C. 154(b) by 0 days.

(21) Appl. No.: 14/834,027

(22) Filed: Aug. 24, 2015

Related U.S. Application Data

(60) Provisional application No. 62/203,748, filed on Aug. 11, 2015.

(51) Int. Cl.
*A61K 31/437* (2006.01)

(52) U.S. Cl.
CPC .................................. *A61K 31/437* (2013.01)

(58) Field of Classification Search
CPC .................................................... A61K 31/437
USPC ......................................................... 514/302
See application file for complete search history.

(56) References Cited

U.S. PATENT DOCUMENTS

| | | | |
|---|---|---|---|
| 4,278,676 A | 7/1981 | Krogsgaard-Larsen |
| 4,353,910 A | 10/1982 | Perregaard |
| 4,362,731 A | 12/1982 | Hill |

FOREIGN PATENT DOCUMENTS

| | | |
|---|---|---|
| WO | WO 2005094820 | 10/2005 |

OTHER PUBLICATIONS

Cheng et al., Anesthesiology (1985), vol. 63(2), pp. 147-151.*
Ebert et al., Pharm. and Therapeut. (2006), vol. 112, pp. 612-629.*
McCaffery et al., Pain: Clin. Manual (1996), pp. 1-10.*
Sessler et al., Semin. Respir. Crit. Care Med. (2013), vol. 34(2), pp. 169-178.*
Walsh et al., Sleep (2007), vol. 30(5), pp. 593-602.*
Stephanie Saul, "Merck Cancels Work on a New Insomnia Medication," The New York Times, Business Day, 2015; http://www.nytimes.com/2007/03/29/business/29sleep.html?_r=0; 3 pages.
Hughes et al., "Sedation in the Intensive Care Setting," Clinical Pharmacology: Advances and Applications; 2012, (Dovepress) vol. 4; pp. 53-63.
Ransdell Pierson, "UPDATE 2-Merck, Lundbeck scrap insomnia drug after trials," Rueters, (Dow Jones); 2015; 2 pages.

* cited by examiner

*Primary Examiner* — Taofiq A Solola
(74) *Attorney, Agent, or Firm* — Carter, DeLuca, Farrell & Schmidt, LLP

(57) ABSTRACT

Methods of sedating a patient undergoing critical care treatment using intravenous gaboxadol are provided.

10 Claims, No Drawings

METHODS OF SEDATION DURING CRITICAL CARE TREATMENT

CROSS-REFERENCE TO RELATED APPLICATIONS

This application claims the benefit of, and priority to, U.S. Provisional Patent Application No. 62/203,748, filed on Aug. 11, 2015, the entire contents of which are hereby incorporated herein by reference.

TECHNICAL FIELD

Methods of sedating a patient undergoing critical care treatment using gaboxadol or a pharmaceutically acceptable salt thereof are provided.

BACKGROUND

Critically ill patients are routinely provided analgesia and sedation to prevent pain and anxiety during invasive procedures. There is currently no universally accepted sedative regimen for critically ill patients. Thus, patients often receive a variety of drugs during their stay in an intensive care unit, often receiving a variety of drugs concurrently. Moreover, over sedation may occur leading to longer time on mechanical ventilation, prolonged stay in the intensive care unit, and increased brain dysfunction (e.g., delirium and coma). For many years, sedation guidelines have supported the use of gamma-aminobutyric-acid (GABA)-receptor agonists, including propofol and benzodiazepines (e.g., midazolam) for targeted sedation of ICU patients. However, these agents are associated with adverse effects such as respiratory depression, hypotension, bradycardia, hyperlipidemia, lack of orientation, and potential abuse. Accordingly, there remains a need in the art for safe and effective methods of sedating a patient undergoing critical care treatment.

Gaboxadol (4,5,6,7-tetrahydroisoxazolo [5,4-c]pyridine-3-ol) (THIP)), described in U.S. Pat. Nos. 4,278,676, 4,362,731, 4,353,910, and WO 2005/094820, is a selective $GABA_A$ receptor agonist with a preference for δ-subunit containing $GABA_A$ receptors. In the early 1980s gaboxadol was the subject of a series of pilot studies that tested its efficacy as an analgesic and anxiolytic, as well as a treatment for tardive dyskinesia, Huntington's disease, Alzheimer's disease, and spasticity. In the 1990s gaboxadol moved into late stage development for the treatment of insomnia but failed to show significant effects in sleep onset and sleep maintenance in a three-month efficacy study. Additionally, patients with a history of drug abuse who received gaboxadol experienced a steep increase in psychiatric adverse events. As a result of these negative results the development of gaboxadol was terminated. It has now been found that gaboxadol may provide a safe and effective alternative for the sedation of patients undergoing critical care treatment.

SUMMARY

Provided herein are methods of critical care sedation of a patient by administering to the patient a pharmaceutical composition of gaboxadol or a pharmaceutically acceptable salt thereof.

DETAILED DESCRIPTION

Provided herein are methods of critical care sedation of a patient by administering to the patient a pharmaceutical composition of gaboxadol or a pharmaceutically acceptable salt thereof. Critical care sedation herein includes, but is not limited to, intensive care sedation; sedation of the patient prior to or during surgery; procedural sedation; monitored anesthesia care; combined sedation and regional anesthesia; induction of general anesthesia; maintenance of general anesthesia; initiation of monitored anesthesia care; maintenance of monitored anesthesia care; general anesthesia; moderate sedation; and conscious sedation. Thus, embodiments include methods of critical care sedation by administering to the patient a pharmaceutical composition of gaboxadol or a pharmaceutically acceptable salt thereof wherein the critical care sedation is selected from the group selected from intensive care sedation, sedation of the patient prior to or during surgery, procedural sedation, monitored anesthesia care, general anesthesia, moderate sedation, and conscious sedation.

In embodiments, critical care sedation herein includes Intensive Care Unit (ICU) sedation. ICU sedation is typically administered to patients to help the patient sleep but still be able to respond to nursing staff (e.g., light sedation). In embodiments, critical care sedation herein involves procedural sedation. In embodiments, the methods involve sedation of initially intubated and mechanically ventilated patients during treatment in an intensive care setting. In embodiments, the methods include sedation of non-intubated patients prior to and/or during surgical and other procedures.

In embodiments, critical care sedation herein involves Moderate Sedation or Conscious Sedation. During Moderate Sedation or Conscious Sedation a physician supervises or personally administers sedative and/or analgesic medications that can allay patient anxiety and control pain during a diagnostic or therapeutic procedure. Such drug-induced depression of a patient's level of consciousness to a "moderate" level of sedation, as defined in the Joint Commission standards, is intended to facilitate the successful performance of the diagnostic or therapeutic procedure while providing patient comfort and cooperation.

In embodiments, critical care sedation involves Monitored Anesthesia Care. Monitored Anesthesia Care (MAC) is a specific anesthesia service that involves an anesthesiologist administering sedatives and analgesics to a patient while monitoring his/her vital signs. Monitored Anesthesia Care is often used to supplement local and regional anesthesia for non-intubated patients undergoing non-invasive procedures and minor surgery. The goal of Monitored Anesthesia Care is to relieve anxiety by inducing a minimally depressed level of consciousness while the patient is able to continuously and independently maintain an open airway and to respond appropriately to verbal commands.

An important component of MAC is the anesthesia assessment and management of a patient's actual or anticipated medical problems that may occur during a diagnostic or therapeutic procedure. While Monitored Anesthesia Care may include the administration of sedatives and/or analgesics often used for Moderate Sedation, the provider of MAC must be prepared and qualified to convert to general anesthesia when necessary. By contrast, Moderate Sedation is not expected to induce depths of sedation that could impair the patient's ability to maintain the integrity of his or her airway.

The administration of sedatives, hypnotics, analgesics, as well as anesthetic drugs commonly used for the induction and maintenance of general anesthesia is often, but not always, a part of Monitored Anesthesia Care. In some patients who may require only minimal sedation, MAC is often indicated because even small doses of these medications could precipitate adverse physiologic responses that would necessitate acute clinical interventions and resuscitation.

The precise amount of gaboxadol administered herein is dependent on numerous factors, such as the general condition of the patient, the condition to be treated, the desired duration of use, the route of administration, etc. The amount of gaboxadol may also be dependent on whether the sedation includes a single administration of gaboxadol to achieve sedation or a combination of an initiation dosage to achieve sedation and a maintenance dosage to continue sedation in the patient. Thus, the amount of gaboxadol used may be dependent on whether the administration is during an initiation dosage or a maintenance dosage. In embodiments, the methods involve administration of a single initiation dosage to provide critical care sedation. In embodiments, the methods involve administration of an initiation dosage followed by administration of a maintenance dosage to continue critical care sedation. As used herein an initiation dosage may also be referred to as a loading dosage that is administered as an initial higher dose of gaboxadol and may be given at the beginning of treatment before dropping down to a lower maintenance dose. The maintenance dosage may be administered immediately following the initiation dosage or may be separated by a period of time, e.g., 1 minute, 5 minutes, 10 minutes, 15 minutes etc.

The initiation and/or the maintenance dosage of gaboxadol may be provided in one or more administrations to provide the desired amount of sedation. In embodiments, a bolus dose may be used to administer an initiation dosage. In embodiments, one or more intermittent bolus doses may be used to administer a maintenance dose. In embodiments, a bolus dose may be used to administer an initiation dosage and treatment continued by a steady maintenance infusion. In embodiments, a maintenance dosage may be administered by adjusting the rate of intravenous administrations to one or more administration rates described below.

In embodiments, deuterated gaboxadol may be used. Deuteration of pharmaceuticals to improve pharmacokinetics (PK), pharmacodynamics (PD), and toxicity profiles, has been demonstrated previously with some classes of drugs. Accordingly the use of deuterium enriched gaboxadol is contemplated and within the scope of the methods and compositions described herein. Deuterium can be incorporated in any position in replace of hydrogen synthetically, according to the synthetic procedures known in the art. For example, deuterium may be incorporated to various positions having an exchangeable proton, such as the amine N—H, via proton-deuterium equilibrium exchange. Thus, deuterium may be incorporated selectively or non-selectively through methods known in the art to provide deuterium enriched gaboxadol. See Journal of Labeled Compounds and Radiopharmaceuticals 19(5) 689-702 (1982).

Deuterium enriched gaboxadol may be described by the percentage of incorporation of deuterium at a given position in the molecule in the place of hydrogen. For example, deuterium enrichment of 1% at a given position means that 1% of molecules in a given sample contain deuterium at that specified position. The deuterium enrichment can be determined using conventional analytical methods, such as mass spectrometry and nuclear magnetic resonance spectroscopy. In embodiments deuterium enriched gaboxadol means that the specified position is enriched with deuterium above the naturally occurring distribution (i.e., above about 0.0156%). In embodiments deuterium enrichment is no less than about 1%, no less than about 5%, no less than about 10%, no less than about 20%, no less than about 50%, no less than about 70%, no less than about 80%, no less than about 90%, or no less than about 98% of deuterium at a specified position.

In embodiments, the total amount of gaboxadol administered during the critical care sedation is between about 0.1 mg to about 500 mg gaboxadol. For example, the patient may be administered an initiation dose of gaboxadol of between about 1 mg to about 100 mg and then a maintenance dose of between about 1 mg to about 400 mg over a specific period of time, e.g., 20 minutes, 30 minutes, 45 minutes, 1 hour, 6 hours, 12 hours, 24 hours, such that the patient receives a total amount of gaboxadol of between about 1 mg to about 500 mg gaboxadol.

In embodiments, the initiation dose of gaboxadol during critical care sedation may be administered intravenously by infusion or by slow injection. In embodiments, the initiation dose may be administered as a bolus dose. The initiation dosage may involve administering between about 1 mg to about 100 mg gaboxadol. In embodiments, the initiation dosage includes administering an amount of gaboxadol or pharmaceutically acceptable salt thereof between about, e.g., 0.1 mg to 50 mg, 0.1 mg to 25 mg, 0.1 mg to 15 mg, 0.1 mg to 10 mg, or 0.1 mg to 5 mg. In embodiments, the initiation dosage includes administering between about, e.g., 1 mg to 25 mg, 1 mg to 15 mg, 1 mg to 10 mg, or 1 mg to 5 mg.

In examples, the initiation dosage involves about 1 mg, about 2 mg, about 5 mg, about 10 mg, about 25 mg, about 50 mg or increments thereof of gaboxadol. In examples, the initiation dosage involves about 3 mg, about 4 mg, about 7.5 mg, about 12 mg, about 15 mg, about 20 mg, about 30 mg, about 40 mg, or increments thereof of gaboxadol. In examples, the initiation dosage may involve about 60 mg, about 65 mg, about 75 mg, about 80 mg, about 90 mg, or about 100 mg of gaboxadol. In embodiments, the initiation dosage may involve administering gaboxadol to the patient in increments of about 0.5, about 1 mg, about 2 mg, about 2.5 mg, about 5 mg, about 10 mg, or about 20 mg until the desired level of sedation is achieved.

The dose range of gaboxadol administered according to the disclosure herein may also be defined according to one or more pharmacokinetic parameters. In embodiments, the initiation dosage administered during critical care sedation may provide an in vivo plasma profile in the patient of a $C_{max}$ less than, e.g., about 3500 ng/ml, about 3000 ng/ml, about 2500 ng/ml, about 2000 ng/ml, about 1500 ng/ml, or about 1000 ng/ml. In embodiments, the initiation dosage administered during critical care sedation may provide an in vivo plasma profile in the patient of a $C_{max}$ less than, e.g., about 3250 ng/ml, about 2750 ng/ml, about 2250 ng/ml, about 1750 ng/ml, about 1250 ng/ml, or about 750 ng/ml. In embodiments, the initiation dosage may provide an in vivo plasma profile in the patient of a $C_{max}$ less than, e.g., about 1000 ng/ml, about 750 ng/ml, about 250 ng/ml, about 150 ng/ml, about 100 ng/ml, or about 75 ng/ml. In embodiments, the initiation dosage may provide an in vivo plasma profile in the patient of a $C_{max}$ less than about 500 ng/ml. In embodiments, the initiation dosage may provide an in vivo plasma profile in the patient of a $C_{max}$ less than about 350 ng/ml.

In embodiments, the initiation dosage administered during critical care sedation may provide an in vivo plasma profile in the patient of a $AUC_{0-\infty}$ less than, e.g., about 4000 ng·hr/ml, about 3000 ng·hr/ml, about 2500 ng·hr/ml, about 2000 ng·hr/ml, about 1500 ng·hr/ml, about 1000 ng·hr/ml, or about 500 ng·hr/ml. In embodiments, the initiation dosage may provide an in vivo plasma profile of a $AUC_{0-\infty}$ less than about 2250 ng·hr/ml. In embodiments, the initiation dosage may provide an in vivo plasma profile of a $AUC_{0-\infty}$ less than about 1750 ng·hr/ml.

In embodiments, the initiation dose of gaboxadol may be administered at an infusion rate of between about 0.1 to about 1000 µg/kg/hour. In embodiments, the initiation dose may be administered at an infusion rate of between, e.g., about 1 to about 750 µg/kg/min, about 1 to about 500 µg/kg/min, about 1 to about 250 µg/kg/min, about 1 to about 100 µg/kg/min, or about 1 to about 50 µg/kg/min. In other embodiments, the initiation dose may be administered at an infusion rate of between, e.g., about 0.5 to about 250 µg/kg/min, about 0.5 to about 100 µg/kg/min, about 0.5 to about 50 µg/kg/min, or about 0.5 to about 25 µg/kg/min. In embodiments, the initiation dose may be administered at an infusion rate of between, e.g., about 0.25 to about 100 µg/kg/min, about 0.25 to about 75 µg/kg/min, about 0.25 to about 50 µg/kg/min, or about 0.25 to about 25 µg/kg/min.

In embodiments, the initiation dose may be administered at an infusion rate of between about 25 to about 75 µg/kg/min. In embodiments, the initiation dose may be administered at an infusion rate of between about 5 to about 50 µg/kg/min. In embodiments, the infusion rate may be increased by increments of about 5 to 10 µg/kg/min until a desired level of sedation is achieved.

One skilled in the art will appreciate that the infusion rates may also be expressed as mg/kg/h. For example, in embodiments, the initiation dose may be administered at an infusion rate of between about 1 to about 10 mg/kg/h, about 2 to about 10 mg/kg/h, about 5 to about 10 mg/kg/h, or about 8 to about 10 mg/kg/h. In embodiments, the initiation dose may be administered at an infusion rate of between about 2 to about 8 mg/kg/h, about 4 to about 8 mg/kg/h, about 5 to about 8 mg/kg/h, or about 6 to about 10 mg/kg/h. In embodiments, the initiation dose may be administered at an infusion rate of between about 6 to about 9 mg/kg/h (100 to 150 µg/kg/min).

In embodiments the initiation dose of gaboxadol may be administered to achieve a plasma concentration of, e.g., about 0.1 to about 25 µg/kg, about 0.1 to about 15 µg/kg, about 0.1 to about 10 µg/kg, about 0.1 to about 5 µg/kg, about 0.2 to about 2 µg/kg, about 0.5 to about 2 µg/kg, or about 0.5 to about 1 µg/kg. In embodiments, the initiation dose may be administered to achieve a plasma concentration of less than about 15 µg/kg, less than about 10 µg/kg, less than about 5 µg/kg, less than about 2.5 µg/kg, or less than about 1.0 µg/kg of gaboxadol.

In embodiments, the methods provide administration of a maintenance dose of gaboxadol to provide sedation to the patient. One skilled in the art will appreciate that the maintenance dose is dependent on numerous factors, such as the general condition of the patient, the route of administration (e.g., infusion, slow injection, bolus etc.) and the type of critical care sedation. In embodiments the initiation dosage is provided for a period of time, e.g., over 1 minute, 2 minutes, 3 minutes, 5 minutes, 10 minutes etc., followed by a maintenance dosage. The maintenance dosage may be administered immediately following the initiation dosage or separated by a period of time, e.g., 1 minute, 2 minutes, 5 minutes, 10 minutes, 15 minutes. In embodiments, the maintenance dosage may be provided for up to a specific period of time, e.g., up to 1 hour, up to 6 hours, up to 12 hours, or up to 24 hours.

In embodiments, the maintenance dose may be administered by infusion or by slow injection. In embodiments, the maintenance dose of gaboxadol may be administered as an intermittent bolus dose. The maintenance dosage may include administering between about 1 mg to about 100 mg gaboxadol. In embodiments, the maintenance dosage includes administering an amount of gaboxadol or pharmaceutically acceptable salt thereof between about, e.g., 0.1 mg to 50 mg, 0.1 mg to 25 mg, 0.1 mg to 15 mg, 0.1 mg to 10 mg, or 0.1 mg to 5 mg. In embodiments, the maintenance dosage includes administering between about, e.g., 1 mg to 25 mg, 1 mg to 15 mg, 1 mg to 10 mg, or 1 mg to 5 mg.

In examples, a maintenance dosage may include administering, e.g., about 1 mg, about 2 mg, about 5 mg, about 10 mg, about 25 mg, about 50 mg or increments thereof of gaboxadol. In examples, a maintenance dosage may include administering about 3 mg, about 7.5 mg, about 12 mg, about 15 mg, about 20 mg, about 30 mg, about 40 mg, or increments thereof of gaboxadol or pharmaceutically acceptable salt thereof. In examples, a maintenance dosage may include administering about 60 mg, about 65 mg, about 75 mg, about 80 mg, about 90 mg, or about 100 mg of gaboxadol. In embodiments, the maintenance dosage may include administering gaboxadol to the patient in increments of about 0.5 mg, 1 mg, 5 mg, about 10 mg, about 20 mg, about 25 mg, or about 50 mg.

The maintenance dosage of gaboxadol administered herein may also be defined according to one or more pharmacokinetic parameters. In embodiments, plasma concentrations of gaboxadol for maintenance of sedation can be achieved by adjusting the rate of intravenous administration or by administering intermittent bolus injections. In embodiments, the maintenance dosage administered during critical care sedation may provide an in vivo plasma profile in the patient of a $C_{max}$ less than, e.g., about 3500 ng/ml, about 3000 ng/ml, about 2500 ng/ml, about 2000 ng/ml, about 1500 ng/ml, or about 1000 ng/ml. In embodiments, the maintenance dosage may provide an in vivo plasma profile in the patient of a $C_{max}$ less than, e.g., about 3250 ng/ml, about 2750 ng/ml, about 2250 ng/ml, about 1750 ng/ml, about 1250 ng/ml, or about 750 ng/ml. In embodiments, the maintenance dosage may provide an in vivo plasma profile in the patient of a $C_{max}$ less than, e.g., about 1000 ng/ml, about 750 ng/ml, about 250 ng/ml, about 150 ng/ml, about 100 ng/ml, or about 75 ng/ml. In embodiments, the maintenance dosage may provide an in vivo plasma profile in the patient of a $C_{max}$ less than about 500 ng/ml. In embodiments, the maintenance dosage may provide an in vivo plasma profile in the patient of a $C_{max}$ less than about 250 ng/ml.

In embodiments, the maintenance dosage administered during critical care sedation may provide an in vivo plasma profile in the patient of an $AUC_{0-\infty}$ less than, e.g., about 4000 ng·hr/ml, about 3000 ng·hr/ml, about 2500 ng·hr/ml, about 2000 ng·hr/ml, about 1500 ng·hr/ml, about 1000 ng·hr/ml, or about 500 ng·hr/ml. In embodiments, the maintenance dosage provides an in vivo plasma profile of a $AUC_{0-\infty}$ less than about 2250 ng·hr/ml. In embodiments, the maintenance dosage may provide an in vivo plasma profile in the patient of a $AUC_{0-\infty}$ less than about 1750 ng·hr/ml.

In embodiments, the maintenance dose may be administered at an infusion rate of between about 0.1 to about 1000 µg/kg/hour. In embodiments, the maintenance dose may be administered at an infusion rate of between, e.g., about 1 to about 750 µg/kg/min, about 1 to about 500 µg/kg/min, about 1 to about 250 µg/kg/min, about 1 to about 100 µg/kg/min, or about 1 to about 50 µg/kg/min. In embodiments, the maintenance dose may be administered at an infusion rate of between, e.g., about 0.5 to about 250 µg/kg/min, about 0.5 to about 100 µg/kg/min, about 0.5 to about 50 µg/kg/min, or about 0.5 to about 25 µg/kg/min. In embodiments, the maintenance dose may be administered at an infusion rate of between, e.g., about 0.25 to about 100 µg/kg/min, about 0.25 to about 75 µg/kg/min, about 0.25 to about 50 µg/kg/min, or about 0.25 to about 25 µg/kg/min.

In embodiments, the maintenance dose may be administered at an infusion rate of between about 25 to about 75 µg/kg/min. In embodiments, the maintenance dose may be administered at an infusion rate of between about 5 to about 50 μg/kg/min. In embodiments, the infusion rate may be increased by increments of about 5 to 10 μg/kg/min to maintain the desired level of sedation. One skilled in the art will appreciate that the infusion rates described may also be expressed as mg/kg/h. For example, in embodiments, the maintenance dose may be administered at an infusion rate of between about 1 to about 10 mg/kg/h, about 2 to about 10 mg/kg/h, about 5 to about 10 mg/kg/h, or about 8 to about 10 mg/kg/h. In embodiments, the maintenance dose may be administered at an infusion rate of between about 2 to about 8 mg/kg/h, about 4 to about 8 mg/kg/h, about 5 to about 8 mg/kg/h, or about 6 to about 10 mg/kg/h. In embodiments, the maintenance dose may be administered at an infusion rate of between about 6 to about 9 mg/kg/h (100 to 150 μg/kg/min).

In embodiments the maintenance dose may be administered to maintain a plasma concentration range of the patient of, e.g., about 0.1 to about 25 μg/kg, about 0.1 to about 15 μg/kg, about 0.1 to about 10 μg/kg, about 0.1 to about 5 μg/kg, about 0.2 to about 2 μg/kg, about 0.5 to about 2 μg/kg, or about 0.5 to about 1 μg/kg of gaboxadol. In exemplary embodiments, the maintenance dose may be less than, e.g., about 5 μg/kg, less than about 2.5 μg/kg, or less than about 1.0 μg/kg of gaboxadol.

In embodiments, gaboxadol is continuously infused in mechanically ventilated patients prior to extubation, during extubation, and post-extubation. In embodiments, sedation is provided wherein the infusion does not last longer than, e.g., 6 hours, 12 hours or 24 hours. In specific examples, the methods provide infusion wherein the infusion does not last more than 24 hours. In embodiments, gaboxadol is administered using a controlled infusion device. In embodiments, the gaboxadol is co-administered with an anesthetic, sedative, hypnotic, or opioid. Such co-administration may lead to an enhancement of effects or synergistic effect resulting in increased sedative activity. If observed, reduction in dosage of the amount of gaboxadol or the concomitant anesthetic, sedative, hypnotic, or opioid may be required.

One skilled in the art will appreciate that there are numerous animal models that may be used to evaluate and compare the relative safety and efficacy of pharmaceutical products. Accordingly, using a relevant animal model, one skilled in the art may be able to compare the safety and/or effectiveness of gaboxadol relative to other sedatives. For example, tests of preattentive functioning have been described for mice that utilize a simple testing paradigm called prepulse inhibition (PPI). Additional paradigms include simple screens using object discrimination tests or more complex paradigms such as go/no-go testing, five-choice serial attention tasks, or latent inhibition. In addition, tests of learning and memory can be designed to assess more specific areas of functioning, including associative learning, nonspatial or spatial learning, short- and long-term memory, as well as neurologically specific deficits as revealed by fear or eyelid conditioning.

One skilled in the art would expect compounds that act as GABA agonists to provide similar efficacy and adverse event profiles. Thus, methods herein that provide improvements in sedation and/or reduction in one or more adverse events may be considered surprising and unexpected. Accordingly, in embodiments gaboxadol may be administered wherein the methods surprisingly and unexpectedly provide increased efficacy and/or reduced adverse events observed during critical care sedation. For example, the methods described herein may provide decreased incidence of an adverse event selected from the group consisting of respiratory depression, hypotension, bradycardia, hyperlipidemia and lack of orientation.

Moreover, it is known in the art that sedation methods may also lead to adverse events that occur after sedation or may be caused alone or in part from sedative use. For example, patients that are administered sedatives may experience longer time on mechanical ventilation, prolonged stay in the intensive care unit, and/or increased brain dysfunction (e.g., delirium and coma). In embodiments, the methods may surprisingly and unexpectedly provide increased efficacy and/or reduced adverse events after critical care sedation. In embodiments, critical care sedation is provided wherein the administration of gaboxadol provides increased efficacy and/or reduced side effects relative to one or more sedatives. For example, critical care sedation may be provided wherein the administration of gaboxadol provides reduced adverse events compared to another GABA agonist. In other examples, the administration of gaboxadol may provide reduced adverse events compared to propofol. In still other examples, the administration of gaboxadol may provide reduced adverse events compared to midazolam. In embodiments, critical care sedation is provided wherein the administration of gaboxadol provides reduced adverse events compared to dexmedetomidine. In embodiments, the patient may be administered a pharmaceutical composition including gaboxadol wherein the composition provides sedation while also providing reduced adverse events compared to another GABA agonist.

In embodiments methods of critical care sedation are provided by administering a pharmaceutical composition including gaboxadol wherein there is no significant effect of at least one adverse event selected from the group consisting of respiratory depression, hemodynamics, vasodilation, hypotension, bradycardia, tachycardia, atrial fibrillation, pyrexia, cognition, cognitive function, hypertension, apnea, airway obstruction, sinus arrest, oxygen desaturation, and delirium. Cognition refers to the mental processes involved in gaining knowledge and comprehension, such as thinking, knowing, remembering, judging, and problem solving.

In embodiments, the methods include administering gaboxadol wherein there is no substantial occurrence of at least one adverse event selected from the group consisting of respiratory depression, hemodynamics, vasodilation, hypotension, bradycardia, tachycardia, atrial fibrillation, pyrexia, cognition, cognitive function, hypertension, apnea, airway obstruction, sinus arrest, oxygen desaturation, and delirium. In embodiments, there is no significant occurrence of at least one adverse event selected from the group consisting of respiratory depression, hemodynamics, vasodilation, hypotension, bradycardia, tachycardia, atrial fibrillation, pyrexia, cognition, cognitive function, hypertension, apnea, airway obstruction, sinus arrest, oxygen desaturation, and delirium. In embodiments, the methods include administering gaboxadol wherein there is no statistically significant occurrence of at least one adverse event. For example, the methods may include administering gaboxadol wherein there is no meaningful effect on cognition. In examples, the methods may include administering gaboxadol wherein the patient experiences no significant sinus arrest.

In embodiments, provided herein are methods of critical care sedation of a patient by administering a pharmaceutical composition including gaboxadol wherein respiratory depression is not substantial. In embodiments, administration of gaboxadol to a patient results in reductions in respiratory depression relative to administration of another sedative, e.g., propofol, lorazepam, midazolam, and/or dexmedetomidine. In embodiments, provided herein are methods of critical care sedation wherein the administration results in no significant respiratory depression. Respiratory depression is a major concern with many sedatives (e.g., midazolam, propofol) currently used for MAC. There is clearly an unmet need for a sedative agent that can safely be used during sedation, and especially MAC, in both healthy and high-risk populations with limited adverse side effects. In embodiments, provided herein are methods of attenuating anxiety and/or stress associated with surgery and/or ICU procedures wherein there is no significant occurrence of respiratory depression.

In embodiments, provided herein are methods of critical care sedation of a patient by administering a pharmaceutical composition including gaboxadol wherein administration does not result in significant delirium. Delirium acute brain dysfunction is sudden severe confusion due to rapid changes in brain function. Delirium occurs in 60-80% of ventilated Intensive Care Unit (ICU) patients and is independently associated with prolonged hospital stay, higher cost, a 3-fold increased risk of dying by six months and ongoing neuropsychological dysfunction. Delirium has recently been shown as a predictor of death, increased cost, and longer length of stay in ventilated patients. Sedative and analgesic medications relieve anxiety and pain, but may contribute to patients' transitioning into delirium. Accordingly provided herein are methods of attenuating anxiety and/or stress associated with surgery and/or ICU procedures without causing significant delirium.

Standard use of GABA agonist sedatives, such as lorazepam and propofol, may contribute to ICU delirium and other unwanted clinical outcomes. Provided herein are methods of sedation wherein the prevalence of delirium is less than with other GABA receptor agonists. In embodiments, provided herein are methods of critical care sedation wherein there is a significant reduction of delirium compared to another GABA receptor agonist, e.g., lorazepam, propofol, midazolam. In embodiments, provided herein are methods of critical care sedation wherein the occurrence of delirium is significantly less than compared to another GABA receptor agonist, e.g., lorazepam, propofol, midazolam.

In embodiments, provided herein are methods of critical care sedation of a patient wherein the patient remains arrousable and oriented.

Unless defined otherwise, all technical and scientific terms used herein have the same meanings as commonly understood by one of skill in the art to which the disclosure herein belongs.

Gaboxadol may be formulated for administration to a patient using pharmaceutically acceptable salts including acid addition salts, a zwitter ion hydrate, zwitter ion anhydrate, hydrochloride or hydrobromide salt, or in the form of the zwitter ion monohydrate. Acid addition salts, include but are not limited to, maleic, fumaric, benzoic, ascorbic, succinic, oxalic, bis-methylenesalicylic, methanesulfonic, ethane-disulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic or theophylline acetic acid addition salts, as well as the 8-halotheophyllines, for example 8-bromo-theophylline. In other suitable embodiments, inorganic acid addition salts, including but not limited to, hydrochloric, hydrobromic, sulfuric, sulfamic, phosphoric or nitric acid addition salts may be used. Gaboxadol may be crystalline, such as the crystalline hydrochloric acid salt, hydrobromic acid salt, or the crystalline zwitter ion monohydrate.

The term "about" or "approximately" as used herein means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, preferably up to 10%, more preferably up to 5%, and more preferably still up to 1% of a given value. Alternatively, particularly with respect to biological systems or processes, the term can mean within an order of magnitude, preferably within 5-fold, and more preferably within 2-fold, of a value.

"PK" refers to the pharmacokinetic profile. $C_{max}$ is defined as the highest plasma drug concentration estimated during an experiment (ng/ml). $T_{max}$ is defined as the time when $C_{max}$ is estimated (min). $AUC_{0-\infty}$ is the total area under the plasma drug concentration-time curve, from drug administration until the drug is eliminated (ng·hr/ml). The area under the curve is governed by clearance. Clearance is defined as the volume of blood or plasma that is totally cleared of its content of drug per unit time (ml/min).

As used herein, the term "treating" or "treatment" refers to alleviating, attenuating or delaying the appearance of clinical symptoms of a disease or condition in a subject that may be afflicted with or predisposed to the disease or condition, but does not yet experience or display clinical or subclinical symptoms of the disease or condition. In certain embodiments, treating" or "treatment" may refer to preventing the appearance of clinical symptoms of a disease or condition in a subject that may be afflicted with or predisposed to the disease or condition, but does not yet experience or display clinical or subclinical symptoms of the disease or condition. "Treating" or "treatment" also refers to inhibiting the disease or condition, e.g., arresting or reducing its development or at least one clinical or subclinical symptom thereof. "Treating" or "treatment" further refers to relieving the disease or condition, e.g., causing regression of the disease or condition or at least one of its clinical or subclinical symptoms. The benefit to a subject to be treated may be statistically significant, mathematically significant, or at least perceptible to the subject and/or the physician. Nonetheless, prophylactic (preventive) and therapeutic (curative) treatment are two separate embodiments of the disclosure herein.

"Effective amount" or "therapeutically effective amount" means a dosage sufficient to alleviate one or more symptom of a disorder, disease, or condition being treated, or to otherwise provide a desired pharmacological and/or physiologic effect.

"Pharmaceutically acceptable" refers to molecular entities and compositions that are "generally regarded as safe"—e.g., that are physiologically tolerable and do not typically produce an allergic or similar untoward reaction, such as gastric upset and the like, when administered to a human. In another embodiment, this term refers to molecular entities and compositions approved by a regulatory agency of the federal or a state government, as the GRAS list under section 204(s) and 409 of the Federal Food, Drug and Cosmetic Act, that is subject to premarket review and approval by the FDA or similar lists, the U.S. Pharmacopeia or another generally recognized pharmacopeia for use in animals, and more particularly in humans.

Those skilled in the art will recognize, or be able to ascertain using no more than routine experimentation, many equivalents to the specific embodiments of the subject matter described herein. Such equivalents are intended to be encompassed by the claims.

EXAMPLES

Example 1

Intravenous Tolerability of Gaboxadol

The first part of this study (Part 1) was conducted to assess the intravenous tolerability of gaboxadol. In particular, Part 1 consisted of 8 normal healthy adult subjects who received double-blind administration of single intravenous (IV) doses of gaboxadol (5 mg and 10 mg) or single IV doses of placebo (normal saline) in a fixed sequence, rising dose fashion. A second part of the study (Part 2) was a 6-period crossover that consisted of 10 normal healthy adult subjects who received double-blind administration of 5 single oral doses of gaboxadol (2.5, 5, 10, 15, and 20 mg) randomized across Periods 1 through 5, and then single-dose gaboxadol 10 mg administered intravenously over 60 minutes in Period 6. There was a washout of 4 days between each treatment period.

The study included healthy, male and female subjects between 18 and 45 years of age within 30% of ideal weight. The subjects in Part 1 of the study could be of either gender, but within Part 2 of the study there had to be at least 4 subjects of each gender.

In Part 1 each subject received two single IV doses of isotonic gaboxadol HCl (5 mg and 10 mg) or IV placebo (normal saline). Subjects received each of the 5 oral doses (2.5, 5, 10, 15, and 20 mg) of gaboxadol and a single IV dose of gaboxadol in Treatment Period 6 (10 mg was selected as the IV dose based on the acceptable tolerability demonstrated in Part 1 of the study). The Primary Endpoints included gaboxadol Pharmacokinetics (dose proportionality), absolute bioavailability and tolerability, and safety following IV and oral gaboxadol.

Following single intravenous doses, gaboxadol $AUC_{0-inf}$ and $C_{max}$ increased with increasing dose while the other parameters (CL, $t_{1/2}$, $V_{SS}$, $f_e$, and $CL_R$) were independent of dose. Gaboxadol exhibited moderate systemic clearance (CL) and moderate steady-state volume of distribution ($V_{SS}$). After oral administration, gaboxadol $AUC_{0-inf}$ and $C_{max}$ increased with increasing dose while the other parameters (CL/F, $t_{max}$, $t_{1/2}$, $f_e$, and $CL_R$) were independent of dose. Oral clearance (CL/F) was of similar magnitude following oral administration as that observed after intravenous administration, consistent with the estimated oral bioavailability of 92%. Renal clearance ($CL_R$) was greater than glomerular filtration rate indicating net secretion of gaboxadol.

These results suggest that single dose administration of intravenous gaboxadol doses of 5 and 10 mg, and single dose administration of oral doses of gaboxadol from 2.5 to 20 mg and are generally well tolerated. There were no serious adverse experiences reported, and the most common clinical adverse experiences reported in both parts of the study were somnolence and dizziness.

Example 2

Assessment of Residual Effects Resulting from Gaboxadol Administration

This study was a double blind, double-dummy, randomized, active- and placebo-controlled, single dose, 3-period crossover study, followed by an open-label, single-dose, single period study in healthy elderly male and female subjects. Subjects were randomized to each of 3 treatments (Treatments A, B, and C) to be administered in a crossover manner over the first 3 treatment periods. For Treatment A, subjects received a single dose of gaboxadol 10 mg; for Treatment B, subjects received a single dose of flurazepam 30 mg; and for Treatment C, subjects received a single dose of placebo. Doses were administered orally at bedtime on Day 1. Subjects were domiciled from early in the evening of dosing until ~36 hours post-dose (morning of Day 3) during each treatment period. The subjects who participated in treatment periods 1-3 participated in a fourth treatment period. In this period, a single dose of gaboxadol 10 mg (Treatment D) was administered orally in an open-label manner on the morning of Day 1 for PK of gaboxadol. There was at least a 14-day washout between the doses of consecutive treatment periods. Study participants included healthy, elderly male and female subjects between 65 and 80 years of age, with a Mini Mental Status 24, weighing at least 55 kg. All subjects received 10 mg gaboxadol monohydrate capsules and 30 mg flurazepam (provided as 2×15 mg capsules), matching placebo was provided for both gaboxadol and flurazepam.

The primary endpoints evaluated included pharmacodynamics (measurement of psychomotor performance, memory, attention and daytime sleepiness the following pm dosing), gaboxadol pharmacokinetics, and safety. Gaboxadol (single dose 10 mg) did not show residual effect 9 hours post-dose on the primary endpoints Choice Reaction Time and Critical Flicker Fusion, whereas the active reference Flurazepam (30 mg single dose) showed significant effect on the same tests. In addition, gaboxadol did not show any signs of residual effects on other measurements applied in the study (Multiple Sleep Latency Test (MSLT); Digit Symbol Substitution Test (DSST), Tracking, Memory tests, Body Sway, and Leeds Sleep Evaluation Questionnaire).

Example 3

Study of Driving Performance after Gaboxadol Administration

This study was a double blind, randomized, placebo and active controlled 5 way cross over study to investigate the effect of evening and middle of the night dosing of gaboxadol on driving performance. The study participants included healthy, male and female subjects between 21 and 45 years of age, with a valid drivers license for at least 3 years.

The effects of gaboxadol on driving performance were investigated using real driving on the road setting. Subjects received 15 mg gaboxadol either in the evening prior to going to bed or at 4 am in the middle of the night following a wake-up call. Following a cognitive and psychomotor test battery, the driving test started at 9 am and lasted for one hour. Gaboxadol 15 mg had a clinically relevant impairing effect on driving following middle-of-the-night administration.

Following the evening dose, a statistically significant effect of gaboxadol 15 mg was observed on driving. However, this effect was less than the effect observed at a 0.05% blood alcohol concentration, the concentration limit at which driving is prohibited in most European countries. There was generally a numerically greater effect following zopiclone (7.5 mg) and zolpidem (10 mg) administered in the evening and in the middle of the night, respectively. Both the evening and the middle-of-the-night dose of gaboxadol were well tolerated with the most frequent adverse events being dizziness, nausea and somnolence for the middle-of-the-night treatment and headache and somnolence for the evening treatment.

Subjects on the active reference zopiclone had a numerically greater effect in the same test. There was no effect on memory test, body sway, DSST or critical tracking, whereas zopiclone had effect on several of these tests.

Example 4

Study of Daytime Performance after Sleep Restriction

This study was a 4-night, parallel-group, randomized, double-blind (with in-house blinding), placebo-controlled, fixed-dose study to assess the effects of gaboxadol on daytime performance in healthy adults subjected to a 5-hour sleep restriction. The study included a 2-night single-blind placebo run-in period, a 4-night double-blind treatment period during which sleep was restricted to 5 hours and a 2-night single-blind placebo run-out period. The study included healthy male and female volunteers 18 to <55 years of age.

2-night run-in period: All patients received placebo □
4-night double-blind treatment period: Patients were randomized to gaboxadol 15 mg or matching placebo
2-night run-out period: All patients received placebo The primary endpoints included observations based on the Multiple Sleep Latency Test (MSLT) and Slow Wave Sleep (SWS) assessment. The primary objective was to evaluate the efficacy of gaboxadol (15 mg) compared to placebo in reducing daytime sleep propensity as measured by MSLT. The gaboxadol subjects had significantly less daytime sleepiness during the Sleep Restriction period than did placebo subjects (p=0.047, 1 sided). The MSLT was on average 2.01 minutes longer for subjects treated with gaboxadol (15 mg) than for those with placebo on the last two Sleep Restriction days.

In addition, a secondary objective was to evaluate the efficacy of gaboxadol compared to placebo in increasing the amount of slow wave sleep (SWS) during the last 2 nights of sleep restriction. Subjects receiving gaboxadol experienced significantly more SWS during the Sleep Restriction period than did placebo subjects (p<0.001, 1 sided). Moreover, subjects treated with gaboxadol on average had 20.53 minutes of SWS longer than those treated with placebo on the last two Sleep Restriction nights.

Finally, this study examined the efficacy of gaboxadol compared to placebo during the last 2 nights/days of sleep restriction in: (1) improving memory and attention as assessed by a neurobehavioral battery; (2) reducing subjective sleepiness as measured by the Karolinska Sleepiness Score (KSS); (3) altering sleep parameters (e.g., total sleep time, latency to onset of Slow Wave Sleep (SWS), slow wave activity (SWA); and (4) reducing biological stress typified by increased heart rate variability, and decreased cortisol levels and decreased catecholamine levels, as well as decreased body temperature.

There was a trend towards less subjective daytime sleepiness for the gaboxadol subjects during the Sleep Restriction period as compared with placebo subjects. The Karolinska Sleepiness Score (KSS) was on average 0.68 less for subjects treated with gaboxadol than for those treated with placebo on the last two Sleep Restriction days (p=0.058, 1 sided) as evaluated by a Longitudinal data analysis (LDA) model with adjustment for baseline KSS, gender, and age. A supportive analysis using covariance (ANCOVA) also supports this finding. The effect sizes computed for the neurocognitive battery showed that there was no strong evidence that gaboxadol improves daytime performance. There were no differences between gaboxadol and placebo with respect to biophysiological measures of stress (heart rate variability, cortisol levels, catecholamine levels, body temperature).

Compared with placebo, gaboxadol has a protective effect on reducing daytime sleepiness as measured by the MSLT on the last 2 days of 4-nights of sleep restriction. Compared with placebo, gaboxadol increases the amount of slow wave sleep (SWS) during the last 2 nights of 4-nights of sleep restriction.

Example 5

Prospective Assessment of Delirium and Long-Term Neuropsychological Dysfunction

This study is used to compare sedation and analgesia for ventilated intensive care unit (ICU) patients treated with an alpha2 agonist (e.g., dexmedetomidine) or a GABA-Agonist (e.g., propofol, lorazepam, midazolam, gaboxadol). In particular, this study is used to assess the delirium rates, efficacy of sedation, analgesia and discharge cognitive status of patients that have undergone sedation therapy. The study is also be used to compare clinical outcomes including duration of mechanical ventilation, ICU length of stay and severity of neuropsychological dysfunction at hospital discharge. In addition, the study is used to develop pharmacokinetic and pharmacodynamic models for gaboxadol in ICU patients.

This study may include adult patients admitted to the medical and surgical ICU for critical illnesses requiring mechanical ventilation. The patients may have an expectation of being mechanically ventilated for greater than 24 hours. In this study patients will receive a bolus dose over a specific period of time, e.g., 10 minutes, followed by an infusion of gaboxadol or a comparator drug (e.g., dexmedetomidine, propofol, lorazepam). A comparison of each sedative is established by first setting a "goal" or "target" sedation level as medically indicated using Richmond Agitation-Sedation Scale. The "actual" RASS level may then be measured every 12 hours. Comparisons are made between the actual and target RASS levels to determine the primary outcome measure, which is the accuracy of achieving the target sedation level.

In addition, the duration and severity of delirium is measured using the CAM-ICU every 12 hours. Delirium is said to be present if the patients are responsive to verbal stimulation with eye opening (e.g., RASS −3 or better) and are found to have an acute change or fluctuation in the course of their mental status, inattention, and either disorganized thinking or an altered level of consciousness. Assessments may also include the Johns Hopkins Adapted Cognitive Exam: Cognitive assessment tool Confusion Assessment Method for the Intensive Care Unit, CAM-ICU delirium assessment tool; and/or the time from initiation of study drug to calm, non-anxious state.

Example 6

Prospective Assessment of the Safety and Efficacy of Gaboxadol for Sedation During Monitored Anesthesia Care This study includes adult patients (>18 years of age) that sre classified in American Society of Anesthesiologists (ASA) Physical Status I, II, III, or IV and require Monitored Anesthesia Care in an operating room or procedure room with an anesthesiologist in attendance. The patients would also require an elective surgery/procedure expected to take longer than 30 minutes.

The patient will be administered intravenous gaboxadol and one or more outcome measures will be observed. For example, one such outcome measure may include the percent of patients not requiring rescue sedation based on achieving and/or maintaining an Observer's Assessment of Alertness/Sedation Scale (OAA/S) score<4. Other outcomes that may be observed include measurements of the total amount (mg) of rescue sedation medication (e.g., midazolam, propofol) required to achieve and/or maintain sedation (OAA/S score<4); the time from onset of gaboxadol infusion to first dose of rescue medication (e.g., midazolam, propofol); the percentage of subjects who convert to alternative sedative and/or anesthetic therapy due to failure of treatment with study drug and rescue; the time to recovery and readiness for discharge from Post-Anesthesia Care Unit (PACU); an anesthesiologist assessment of ease of management; the incidence of post-operative nausea and vomiting in the PACU; and/or subject satisfaction and anxiety assessed 24 hours after administration of gaboxadol.

Example 7

Prospective Assessment of the Safety and Efficacy of Gaboxadol for Intensive Care Unit Sedation This study includes adult patients (>18 years of age) being treated in a surgical intensive care unit. All patients may be initially intubated and receive mechanical ventilation. This study is used to evaluate the sedative properties of gaboxadol by comparing the amount of rescue medication (e.g., midazolam or propofol) required to achieve a specified level of sedation (using the standardized Ramsay Sedation Scale) between gaboxadol and placebo from onset of treatment to extubation or to a total treatment duration of 24 hours.

The Ramsay Level of Sedation Scale (RSS) is a test of rousability at six different levels. It lends itself to universal use, not only in the ICU, but wherever sedative drugs or narcotics are given. It can be added to the pain score and be considered the sixth vital sign.

Ramsay Sedation Scale:
1 Patient is anxious and agitated or restless, or both
2 Patient is co-operative, oriented, and tranquil
3 Patient responds to commands only
4 Patient exhibits brisk response to light glabellar tap or loud auditory stimulus
5 Patient exhibits a sluggish response to light glabellar tap or loud auditory stimulus
6 Patient exhibits no response

The invention claimed is:

1. A method of sedating a human patient during treatment in an intensive care setting comprising intravenously administering to the patient a pharmaceutical composition of gaboxadol or a pharmaceutically acceptable salt thereof that provides an in vivo plasma profile comprising a Cmax less than about 3500 ng/ml wherein the patient remains arousable and oriented.

2. The method of claim 1, wherein the patient is undergoing treatment in an intensive care setting and the treatment is selected from the group consisting of intensive care sedation, sedation of the patient prior to surgery, procedural sedation, monitored anesthesia care, moderate sedation and conscious sedation.

3. The method according to claim 1, wherein the patient is undergoing treatment in an intensive care setting and is monitored anesthesia care.

4. The method according to claim 1, wherein the total amount of gaboxadol administered during treatment is between about 0.1 mg to about 500 mg gaboxadol.

5. The method according to claim 1, wherein an initiation dose is administered to the patient that provides an in vivo plasma profile comprising a $AUC_{0-\infty}$ less than about 4000 ng hr/ml.

6. The method according to claim 1, wherein the gaboxadol or a pharmaceutically acceptable salt thereof is administered at an infusion rate of between about 0.1 to about 1000 µg/kg/min.

7. The method according to claim 1, wherein the gaboxadol or a pharmaceutically acceptable salt thereof is administered at an infusion rate of between about 1 to about 750 µg/kg/min.

8. The method according to claim 1, wherein the gaboxadol or a pharmaceutically acceptable salt thereof is administered in an amount less than about 20 µg/kg.

9. The method according to claim 1, wherein the gaboxadol or a pharmaceutically acceptable salt thereof is administered in an amount of about 0.1 to about 25 µg/kg.

10. A method of sedating a human patient during treatment in an intensive care setting comprising:
intravenously administering to the patient a pharmaceutical composition of gaboxadol or a pharmaceutically acceptable salt thereof that provides an in vivo plasma profile comprising a Cmax less than about 3500 ng/ml; and
maintaining the patient in an arousable and oriented state.

* * * * *